United States Patent [19]

Keefer

[11] Patent Number: 4,954,526

[45] Date of Patent: Sep. 4, 1990

[54] STABILIZED NITRIC OXIDE - PRIMARY AMINE COMPLEXES USEFUL AS CARDIOVASCULAR AGENTS

[75] Inventor: Larry K. Keefer, Bethesda, Md.

[73] Assignee: The United States of America as represented by the Department of Health and Human Services, Washington, D.C.

[21] Appl. No.: 316,958

[22] Filed: Feb. 28, 1989

[51] Int. Cl.$^5$ .................... A61K 31/13; A61K 31/20; A61K 31/195; A61K 31/655

[52] U.S. Cl. .................................... 514/611; 514/149; 514/558; 514/563; 514/564; 514/610; 564/112; 564/113

[58] Field of Search ............... 514/645, 610, 615, 824, 514/611, 149, 558, 563, 564

[56] References Cited

U.S. PATENT DOCUMENTS

| | | | |
|---|---|---|---|
| 2,635,978 | 4/1953 | Massengale | 514/499 |
| 2,954,314 | 9/1960 | Metzger | 514/499 |
| 3,153,094 | 10/1984 | Reilly | 260/576 |
| 3,309,373 | 3/1967 | Danzig | 546/6 |
| 3,930,970 | 1/1976 | Barton | 260/397.5 |

FOREIGN PATENT DOCUMENTS

62-0175613 4/1987 Japan .

OTHER PUBLICATIONS

Drago & Karstetter, *The Reaction of NO with Various Primary & Secondary Amines*, Aug. 4, 1960, p. 1819, JACS.
Palmer et al., *Nitric Oxide Release Accounts for the Biological Activity of Endothelium-Derived Relaxing Factor*, Nature, pp. 524-526.
CA 108:68610c, *Red Blood Cells Generate Nitric Oxide from Directly Acting, Nitrogenous Vasodilators*, Kruzyna et al.
Palmer et al., Nature, 317, 524-526, 1987.
Kruszyna et al., Toxicol. and Applied Pharmacol., 91, 429-438, 1987.
Ignarro, The FASEB Journal, 3, 31-36, 1989.
Ignarro et al., J. Pharmacol. and Exper. Theraput., 218(2), 739-749, 1981.
Atston et al., The Journal of Biological Chemistry, 260(7), 4069-4074 and 9948, 1985.
Kubrina et al., Izvestiia Akademii Nauk SSSR.Seriia Biologicheska 6, 844-850, 1988 & Abstract.
Drago, "Free Radicals in Inorganic Chemistry", No. 36, Advances in Chemistry Series, American Chemical Society, Washington, DC, 1962, pp. 143-149.
Weirsdorff et al., Chemical Abstracts, 77: 48034f, 1972.
Fujitsuka et al., Chemical Abstracts, 82: 31108p, 1975.
DeLuca et al., Parenteral Drug Delivery Systems, pp. 238-250 of "Pharmaceutics and Pharmacy Practice", J. B. Lippincott Co., Philadelphia, 1987.
Toissel, ASHP, "Handbook on Injectable Drugs", 4th ed., pp. 622-630, 1986.

*Primary Examiner*—Allen J. Robinson
*Attorney, Agent, or Firm*—Birch, Stewart, Kolasch & Birch

[57] ABSTRACT

A method of treating cardiovascular disorders in a mammal, by administering to said mammal an effective amount of a compound of the formula:

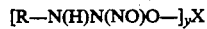

wherein R is loweralkyl, aryl, arylalkyl, or cycloalkyl, any of which R groups may be optionally substituted by one to three substituents selected from the group consisting of: halo, hydroxyl, alkoxy, amino, amido, formyl, carboxyl, or nitro; and wherein X is a pharmaceutically acceptable cation, a pharmaceutically acceptable metal center, or a pharmaceutically acceptable organic group selected from loweralkyl, acyl or amido, and Y is 1 to 3 consistent with the valence of X. Pharmaceutical compositions containing the compounds are also provided.

20 Claims, No Drawings

STABILIZED NITRIC OXIDE - PRIMARY AMINE COMPLEXES USEFUL AS CARDIOVASCULAR AGENTS

BACKGROUND OF THE INVENTION

Numerous nitric oxide nucleophile complexes have been described, e.g. R.S. Drago, *ACS Adv. Chem. Ser.*, Vol. 36, p. 143-149 (1962). Some of these complexes are known to evolve nitric oxide on heating or hydrolysis, e.g., T.J. Hansen, et al., IARC SCI. PUBL., Vol. 41, p. 21-29 (1982); and nitric oxide has been postulated to be identical to endothelium-derived relaxing factor (EDRF) which mediates the action of some vasodilators, R.M.J. Palmer, et al., *Nature*, Vol. 327, p. 524-526 (1987), as well as certain types of intercellular communication in the brain, J. Garthwaite, et al., Nature, Vol. 336, p. 385-388 (1988). The use of nitric oxide-primary amine complexes as biologically active agents has not been previously disclosed.

SUMMARY OF THE INVENTION

One object of the present invention is to provide potent cardiovascular agents useful in treating cardiovascular disorders. The cardiovascular agents provided in the present invention are complexes formed from nitric oxide and primary amines, and esters, ethers, or other derivatives thereof. These nitric oxide-primary amine complexes and esters, ethers or other derivatives regenerate, i.e., release, nitric oxide in vivo, and it is this release of nitric oxide in vivo which accounts for their potent biological activity. Furthermore, since the release rate of nitric oxide from nitric oxide-nucleophile complexes and their esters may vary from almost instantaneous to very slow depending on pH, and other factors such as temperature, a second object of the present invention is to provide stabilized complexes of nitric oxide which release nitric oxide in vivo in an acceptable fashion (as determined by pharmacological testing). A third object of the present invention is to provide pharmaceutical compositions for administering the cardiovascular agents disclosed herein to mammals.

Accordingly, and in consideration of the above objects, the present invention provides a method of treating cardiovascular disorders, wherein said method comprises administering to a mammal, in need thereof, an effective amount of a compound of the formula:

[R-N(H)N(NO)O—]$_y$X

Formula I wherein R is loweralkyl, aryl, arylalkyl, or cycloalkyl, any of which R groups may be substituted by one to three substituents, same or different, selected from halo, hydroxy, alkoxy, amino, amido, formyl, carboxy or nitro; and X is a pharmaceutically acceptable cation,
a pharmaceutically acceptable metal center, or
a pharmaceutically acceptable organic group selected from loweralkyl acyl or amido; and Y is one to three, consistent with the valence of X.

Furthermore, the present invention provides a pharmaceutical composition, comprising:

(I) an effective cardiovascular disorder treating amount of a compound of the formula:

[R-N(H)N(NO)O—]$_y$X

Formula I wherein:

R is loweralkyl, aryl, arylalkyl, or cycloalkyl, any of which R groups may be substituted by one to three substituents, same or different, selected from halo, hydroxy, alkoxy, amino, amido, formyl, carboxy or nitro;

X is a pharmaceutically acceptable cation,
a pharmaceutically acceptable metal center, or
a pharmaceutically acceptable organic group selected from loweralkyl, acyl or amido;

Y is one, two or three, consistent with the valence of X; and (II) a pharmaceutically acceptable carrier therefor.

A glossary of certain terms utilized herein is also provided herewith, in order to remove any vagueness, which may exist as to the meanings of those terms.

The term "loweralkyl" as used herein means branched and straight chain radicals of three to eight carbons inclusive, and is exemplified by such groups as propyl, isopropyl, butyl, 2-butyl, tert. butyl, amyl, isoamyl, hexyl, heptyl, octyl, and the like.

The term "aryl" as used herein means phenyl, naphthyl, pyrrolyl, pyridinyl, quinolinyl, isoquinolinyl, and the like.

The term "arylalkyl" as used herein means an aryl group, as defined herein, substituted by a straight or branched carbon chain radical of one to three carbon atoms inclusive.

The term "cycloalkyl" as used herein means cyclopropyl, cyclopentyl, cyclohexyl, cycloheptyl, cyclooctyl, and the like.

The term "halo" or "halogen" as used herein means a halogen atom selected from fluorine, chlorine, bromine, and iodine.

The term "hydroxy" or "hydroxyl" as used herein means —OH.

The term "amino" as used herein means —NH$_2$.

The term "amido"[as used herein means —C(0)NH$_2$.

The term "formyl" as used herein means —CH(0).

The term "carboxy" as used herein means —C(0)OH.

The term "nitro" as used herein means -NO$_2$.

The term "pharmaceutically acceptable cation" as used herein means any cation biologically compatible in a mammal, and includes alkylammonium cations, e.g. isopropyl ammonium cation and the like; alkali metals, e.g., sodium, potassium, lithium and the like; and alkaline earth metals, e.g., calcium, barium, magnesium and the like. The only essential characteristic of the cation chosen is that it not be biologically incompatible in a mammal.

The term "pharmaceutically acceptable metal center" as used herein means a central metal ion, having a valence of 1 to 3, attached by coordinate links to one or more nonmetal atoms of each of the Y organic groups of Formula I [i.e., R—N(H)N(NO)O—]. Exemplary of such a metal center would be Fe$^{+2}$, or the like, coordinately linked to two oxygen atoms, or at least one oxygen atom and another nonmetalic atom, of each of the Y organic groups of Formula I.

The term "central metal ion" as used herein includes biologically acceptable metal ions selected from: alkali metals such as sodium, potassium, lithium and the like; alkaline earth metals such as calcium, magnesium, barium and the like; transition metals, including iron, copper, nickel, zinc and the like; Group III metals including aluminum and the like; and lanthanide series metals. The only principal requirement, for the central metal ion chosen is biological compatibility, in a mammal.

The term "pharmaceutically acceptable organic group" as used herein refers to those biologically acceptable organic groups which covalently bond to the organic grouping of Formula I [i.e., R—N(H)N-(NO)O—] to form ethers, esters and other derivatives thereof [e.g., R—N(H)N(NO)O—X; wherein X is a biologically acceptable organic group]. Exemplary of such acceptable organic groups are loweralkyl, acyl, amido and the like.

The term "acyl" as used herein means an organic acid group in which the —OH of a carboxyl group is replaced by some other substituent. Exemplary of such acyl groups are —C(O)CH$_3$, —C(O)C$_6$H$_5$ and the like.

The term "alkoxy" as used herein means —O—CH$_3$, —O—CH$_2$H$_5$ —O—loweralkyl.

The term "pharmaceutically acceptable carrier" as used herein means those excipients and carriers known in the pharmaceutical manufacturing art to be acceptable when one wishes to administer a pharmaceutical composition by an intravenous or oral route.

DETAILED DESCRIPTION OF THE INVENTION

The compounds of Formula I are stable nitric oxide-primary amine complexes and their esters, both of which generally release nitric oxide in vivo in a controlled fashion. This controlled release of nitric oxide makes the compounds valuable as pharmaceutical agents; and the same compounds are fully contemplated herein as useful in the treatment of such cardiovascular disorders as hypertension, arteriosclerosis, cerebral vasospasm, and coronary vasospasm.

While all compounds encompassed by Formula I are considered of value in treating cardiovascular disorders and effective in the method of the present invention, generally, it is thought that compounds of Formula I having an R group which is a branched loweralkyl of 3-6 carbons inclusive, substituted or unsubstituted, are most preferred in the present invention; but other Formula I compounds wherein the R groups cycloalkyl or cycloalkylloweralkyl appear, substituted or unsubstituted, are also preferred. Moreover, if one of the above preferred R groups is substituted, it is thought that the most preferable substituents would include one to three, same or different, of the following: halo, hydroxy, amino, formyl or carboxyl groups.

It is also thought that compounds having X as loweralkylammonium cation, alkali metal cation or alkaline earth metal cation are the most preferable to use in the method of the present invention.

It should be understood that Formula I compounds useful in the method of the present invention can be most probably prepared by a variety of chemical synthesis methods known to those skilled in the art, and that the following methods are only exemplary of methods which may be used to prepare Formula I compounds, and that as such they should not be construed to limit the scope of the present invention in any manner.

Nitric oxide-primary amine complexes useful in the method of the present invention may be prepared if desired by the method of R.S. Drago et al, *J. Am. Chem. Soc.*, Vol. 83, p. 1819-1822 (1961). The following is a scheme of the reaction taught by Drago. In the reaction (BNO) is a transition state or intermediate formed in the reaction.

RNH$_2$ +NO→[RNH$_2$NO](BNO)

[RNH$_2$NO]+NO→[RNH$_2$N$_2$O$_2$]

[RNH$_2$N$_2$O$_2$]+RNH$_2$ →RNH$_3$+RNHN$_2$O$_2$$^-$

The above Drago reaction may be carried out by bubbling nitric oxide into a cold (−78° C.) ether solution of the appropriate amine. Pure solid product should precipitate, Drago teaches, and these precipitated products may, if desired, be reprecipitated from chloroform solution with ether. Additionally, high pressure techniques taught by R.S. Drago et al in *J. Am. Chem. Soc.*, Vol. 83, p. 1819-1822 (1961) may be utilized in the above reaction to produce a product in a yield of about 70-80% of theoretical.

When one utilizes the above reaction the X grouping of the complex initially formed is necessarily an ammonium cation, i.e., RNH$_3$$^+$. In order to change the complexes, cation to an alkali metal or alkaline earth metal cation, the following reaction scheme may be utilized. In the reaction M+ is either an alkali metal or alkaline earth metal cation.

RHN$_3$$^{30}$+RNHN$_2$O$_2$$^-$+M$^{+Oet-}$→RHN-$_2$+EtOH+M$^+$+RNHN$_2$O$_2$$^-$

The desired salt thus obtained may be recrystallized from appropriate organic solvents known to those skilled in the art, or simply washed with appropriate solvents, in order to obtain purified product.

Once obtained, the above salts can be converted to covalent metal complex, ether or ester encompassed by Formula I by reaction with an appropriate metal center, alkylating, acylating or carbamoylating agent. Suitable derivatization methods and procedures for preparing the same are generally known to those skilled in the art and the use of such in preparing compounds of Formula I wherein the X group is a biologically acceptable metal center or a biologically acceptable organic group, as defined herein, are fully contemplated.

When the above Drago reaction mechanisms are utilized, certain of the primary amines to be reacted with nitric oxide may contain additional nitrogen, oxygen or other heteroatoms substituted by hydrogen, which one does not desire to react with nitric oxide. In such cases, these hydrogen substituted heteroatoms should be blocked with an appropriate blocking group before reaction with nitric oxide. The blocked heteroatoms may then be unblocked subsequent to the Drago reaction of the primary amine with nitric oxide. Appropriate blocking agents and deblocking agents and methods of using the same are generally known to those skilled in the art, and the use of such in preparing compounds of Formula I wherein an R group is substituted by and/or contains at least one heteroatom substituted by at least one hydrogen atom, is fully contemplated herein.

The following Preparations serve as further illustration of the methods, described herein, which may be utilized to prepare Formula I compounds, and should not be construed to limit the scope of the present invention.

Preparation I

Isooroovlamine - nitric oxide isooroovlammonium salt complex 1:11

(CH$_3$)$_2$CHNH$_3$+O—N(NO)N(H)(—CH(CH$_3$)$_2$)

Utilizing the high pressure reaction method of R.S. Drago, et al., *J. Am. Chem. Soc.*, Vol. 83, p. 1819-1822

(196), the above nitric oxide complex was obtained by reacting a solution of isopropylamine and ether with nitric oxide at a temperature of −78° C. for a period of about 24 hr. The reaction took place under high pressure in a high pressure reaction vessel, and nitric oxide was incorporated into the reaction mixture via a high pressure reservoir. The title compound was obtained in satisfactory yield.

Preparation II

Isopropylamine-nitric oxide sodium salt complex [1:1]

$$Na^+\ ^-O-N(NO)N(H)(-CH(CH_3)_2)$$

Utilizing the method of R.S. Drago, et al., *J. Am. Chem. Soc.* Vol. 83, p. 1819-1822 (1961) the title compound is obtained by reacting a slightly greater than stoichiometric amount of the compound of Preparation I (slurried in ethyl alcohol) with sodium ethoxide. Upon stirring for about 5 minutes, ether is added to the reaction mixture to precipitate the title compound, which may be additionally washed with ether and ethyl alcohol to remove impurities.

Preparation III

Utilizing the procedure of Preparation I, and reacting nitric oxide with solutions of the following loweralkylamines in ethyl ether:
isobutylamine,
n-butylamine, and
2-butylamine,
the following loweralkylamine-nitric oxide ammonium salt complexes are obtained:

$$(CH_3)_2C(H)CH_2NH_3^+\ ^-O-N(NO)N(H)[-CH_2-C(H)(CH_3)_2],$$

$$(n-C_4H_9)NH_3^+\ ^-O-N(NO)N(H)(-n-C_4H_9), \text{ and}$$

$$[(C_2H_5)CH_3)CH]NH_3^+\ ^-O-N(NO)N(H)[-CH(CH_3)(C_2H_5)].$$ Utilizing the procedure of Preparation II, and reacting each of the loweralkylamine-nitric oxide ammonium salt complexes obtained in Preparation III with sodium ethoxide, there are obtained the following loweralkylamine-nitric oxide sodium salt complexes:

$$Na^+\ ^-O-N(NO)N(H)[-CH_2C(H)(CH_3)_2],$$

$$Na^+\ ^-O-N(NO)N(H)(-n-C_4H_9), \text{ and}$$

$$Na^+\ ^-O-N(NO)N(H)[-CH(CH_3)(C_2H_5)].$$

Preparation V

Utilizing the procedure of Preparation I, and reacting each of the following primary amines (in a solution of ethyl ether):
benzylamine,
cyclohexylmethylamine,
cyclohexylamine,
p-methoxyaniline, and
m-bromoaniline,
with nitric oxide, at -78° C for 24 hr under high pressure, there are obtained the following primary amine-nitric oxide ammonium salt complexes:

$$(C_6H_5)CH_2NH_3^+\ ^-O-N(NO)N(H)(-CH_2-C_6H_5),$$

$$(C_6H_{11})CH_2NH_3^+\ ^-O-N(NO)N(H)(-CH_2-C_6H_{11}),$$

$$C_6H_{11}NH_3^+\ ^-O-N(NO)N(H)(-C_6H_{11}),$$

$$[4-(CH_3O)-C_6H_4]NH_3^+\ ^-O-N(NO)N(H)-[4-(CH_3O)C_6H_4-], \text{ and}$$

$$(3-Br-C_6H_4)NH_3^+\ ^-O-N(NO)N(H)(3-Br-C_6H_4-).$$

Preparation VI

Utilizing the procedure of Preparation II, and reacting each of the primary amine-nitric oxide ammonium salts obtained in preparation V, with sodium ethoxide in a slurry of ethyl alcohol, the following compounds are obtained, by precipitation, after addition of ethyl ether:

$$Na^+\ ^-O-N(NO)N(H)(-CH_2-C_6H_5),$$

$$Na^+\ ^-O-N(NO)N(H)(-CH_2-C_6H_{11}),$$

$$Na^+\ ^-O-N(NO)N(H)(-C_6H_{11}),$$

$$Na^+\ ^-O-N(NO)N(H)[4-(CH_3O)-C_6H_4-], \text{ and}$$

$$Na^+\ ^-O-N(NO)N(H)(3-Br-C_6H_4-).$$

Pharmacological Testing

Certain compounds encompassed by the present invention were tested in pharmacological models to determine their activity as cardiovascular agents. Inasmuch as the compounds, pharmacological activity, disclosed herein, is related principally to their ability to release nitric oxide in vivo, the following Examples should not be considered limiting to the number of compounds, disclosed herein, which are useful in the methods of the present invention, since all Formula I compounds are capable of regenerating nitric oxide in vivo. The following examples can and should, however, be assumed to illustrate the general ability of all the Formula I compounds disclosed herein to effectively treat certain cardiovascular disorders such as hypertension, arteriosclerosis, cerebral vasospasm and coronary vasospasm, by way of a controlled release of nitric oxide in vivo.

EXAMPLE 1

A 0.05 M solution of the compound of Preparation I, i.e., $(CH_3)_2CHNH_3^+\ ^-O-N(NO)N(H)(CH(CH_3)_2)$, in normal saline was prepared. Injection of 0.04 ml of this solution over a 30 sec. period into an anesthetized rat (350g) via a catheter in the femoral vein resulted in an immediate drop in blood pressure from 80 to 30 mm Hg, and a compensatory increase in heart rate from 320 to 340/min. The reduced blood pressure remained steady for 10 min. at 30 mm Hg before a perceptible increase could be seen. Full recovery to baseline values had occurred by 30 min after the injection. Later, smaller bolus doses of the compound of Preparation I were also given to the same anesthetized rat and these smaller doses elicited responses similar to those seen with the larger dose. Later still, a 0.0014 M solution of the compound of Preparation I was administered by continuous infusion to the same anesthetized rat at a rate of 1.4 ml/min. Baseline blood pressure was lowered over 10 min. from 105/73 to 83/65 mm Hg. It was also determined during continuous infusion (at the above rate) that the compound of Preparation I had no effect on the action of a 0.5 nmole dose of angiotensin II given to the rat, but that the continuous infusion of the compound of Preparation I (at the above rate) did completely abolish the vasoconstrictor activity of a 0.5 nmole bolus dose of endothelin given to the rat. In view of the above results, it is concluded that the compound of Preparation I is an active cardiovascular agent, and that its actions are predictable and reversible.

EXAMPLE 2 When the compound of Preparation II, i.e., Na$^+$ $^-$O—N(NO)N(H)(—CH(CH$_3$)$_2$) is administered to an anesthetized rat via a catheter as was the compound of Preparation I in Example 1, a similar predictable and reversible reduction in blood pressure is expectable.

EXAMPLE 3 When any of the following Formula I compounds:

(CH$_3$)$_2$C(H)CH$_2$NH$_3$$^+$ $^-$O—N(NO)N(H)[—CH$_2$—C(H)(CH$_3$)$_2$], (n—C$_4$H$_9$—)NH$_3$$^+$ $^-$O—N(NO)N(H)(—n—c$_4$H$_9$),

[(C$_2$H$_5$) (CH$_3$) CH—]NH$_3$$^+$ $^-$O—N(NO)N(H)[—CH(CH$_3$) (C$_2$H$_5$)],

Na$^+$ $^-$ —O—N(NO)N(H)[—CH$_2$—C(H)(CH$_3$)$_2$],

Na$^+$ $^-$O—N(NO)N(H)(—n—C$_4$H$_9$),

Na$^+$ $^-$O—N(NO)N(H)[—CH(CH$_3$)(C$_2$H$_5$)], (C$_6$H$_5$)CH$_2$NH$_3$$^+$ $^-$O—N(NO)N(H)(—CH$_2$—C$_6$H$_{11}$)), (C$_6$H$_{11}$)NH$_3$$^+$ $^-$O—N(NO)N(H)(—CH$_2$—(C$_6$H$_{11}$)), (C$_6$H$_{11}$)NH$_3$$^+$ $^-$O—N(NO)N(H)(—C$_6$H$_{11}$),

[4—(CH$_3$O)—C$_6$H$_4$]NH$_3$$^+$ $^-$O—N(NO)N(H)-[4—(CH$_3$O)C$_6$H$_4$—], (3—Br—C$_6$H$_4$)NH$_3$$^+$ $^-$O—N(NO)N(H)(3—Br—C$_6$H$_4$—),

Na$^+$ $^-$O—N(NO)N(H)(—CH$_2$(C$_6$H$_5$)),

Na$^+$ $^-$O—N(NO)N(H)(—CH$_2$(C$_6$H$_{11}$)),

Na$^+$ $^-$O—N(NO)N(H)(—C$_6$H$_{11}$),

Na$^+$ $^-$O—N(NO)N(H)[4—(CH$_3$O)C$_6$H$_4$—], or

Na$^+$ $^-$O—N(NO)N(H)(3—Br—C$_6$H$_4$—)

are administered, either separately or in combination, to an anesthetized rat via a catheter as was the compound of Preparation I in Example 1, a similarly predictable and reversible reduction in blood pressure is expectable.

EXAMPLE 4

When any of the compounds encompassed by Formula I, herein, is administered to an anesthetized rat by the methods provided herein in Example 1, it is predictable that a similar reduction in blood pressure will occur, due to in vivo release of nitric oxide by the Formula I compounds utilized.

Pharmaceutical Compositions

Due to their chemical structures, the compounds of the present invention wherein X is a pharmaceutically acceptable cation are most preferably administered by intravenous injection, those compounds of Formula I wherein X is a pharmaceutically acceptable metal center or an organic group are preferably administered either intravenously or orally. Preferably, the compounds of the present invention are made into pharmaceutical injectable or oral compositions by combination with appropriate pharmaceutically acceptable carriers or diluents. Furthermore, while Formula I compounds provided herein may be formulated into injectable preparations and oral preparations in ways usual for these routes of administration, and the following methods and excipients are exemplary of usual and acceptable means, they should not be considered to limit the scope of the present invention with respect to pharmaceutical compositions.

The compounds of the present invention may be formulated into preparations for injections by dissolving, suspending, or emulsifying them in an aqueous or non-aqueous solvent, such as vegetable oil, synthetic aliphatic acid glycerides, esters of higher aliphatic acids or propylene glycol; and if desired, with conventional additives such as solubilizers, isotonic agents, suspending agents, emulsifying agents, stabilizers and preservatives. Parenteral administration of the compounds of the present invention may also be had by a pharmaceutically acceptable carrier such as dextrose, sterile water for injection, USP, or by normal saline.

In the case of oral preparations, the compounds may be used alone or in combination with appropriate additives to make tablets, powders, granules or capsules, e.g., with conventional additives such as lactose, mannitol, corn starch or potato starch; with binders such as crystalline cellulose, cellulose derivatives, acacia, corn starch or gelatins; with disintegrators such as corn starch, potato starch or sodium carboxymethylcellulose; with lubricants such as talc or magnesium stearate; and if desired, with diluents, buffering agents, moistening agents, preservatives and flavoring agents.

The amount of the compounds of the present invention to be used as cardiovascular agents of course varies according to the type of cardiovascular disorder encountered and the route of administration chosen. A suitable dosage is thought to be about 0.01 to 10.0 mg/kg/day body weight where one is treating hypertension, arteriosclerosis, cerebral vasospasm or coronary vasospasm and the route of administration is intravenous. The preferred dosage is of course that amount just sufficient to treat a particular cardiovascular disorder and would preferably be an amount from about 0.05 to 5.0 mg/kg/day.

It should be understood that the scope of the present invention is only limited by the appended claims.

What is claimed is:

1. A method of treating hypertension, wherein said method comprises administering to a mammal, in need thereof, a therapeutically effective amount of a compound of the formula:

[R—N(H)N(NO)O—]$_y$X wherein:

R is C$_{2-8}$ lower alkyl, phenyl, benzyl, or C$_{3-8}$ cycoloalkyl, any of which R groups may be substituted by one to three substituents, same or different, selected from the group consisting of halo, hydroxy, C$_{1-8}$ alkoxy, —NH$_2$, —C(O)NH$_2$, —CH(O), —C(O)OH and —NO$_2$:

X is a pharmaceutically acceptable cation, a pharmaceutically acceptable metal center, or a pharmaceutically acceptable organic group selected from the group consisting of C$_{1-8}$ lower alkyl, —C(O)CH$_3$ and —C(O)NH$_2$; and Y is one to three, consistent with the valence of X.

2. The method of claim 1, wherein R is branched chain lower alkyl group of 3–6 carbon length, optionally substituted by one to three substituents, same or different, selected from the group consisting of halo, —NH$_2$, hydroxy, —CH(O) and —C(O)OH.

3. The method of claim 1, wherein R is C$_{3-8}$ cycloalkyl, optionally substituted by one to three substituents, same or different, selected from the group consisting of halo, —NH$_2$, hydroxy, —CH(CO) and —C(O)OH.

4. The method of claim 1, wherein R is isopropyl.

5. The method of claim 1, wherein said compound is administered by intravenous injection.

6. The method of claim 1, wherein R is isopropyl; and wherein said compound is administered by intravenous injection.

7. The method of claim 1, wherein X is a pharmaceutically acceptable cation.

8. The method of claim 7, wherein R is branched chain lower alkyl group of 3–6 carbon length, optionally substituted by one to three substituents, same or different, selected from the group consisting of halo, —NH$_2$, hydroxy, —CH(O) and —C(O)OH.

9. The method of claim 7, wherein R is isopropyl.

10. The method of claim 7, wherein R is isopropyl; and wherein said compound is administered by intravenous injection.

11. A pharmaceutical composition comprising:
(I) a therapeutically effective hypertension treating amount of a compound of the formula:

[R—N(H)N(NO)O—]$_y$X wherein:
R is C$_{3-8}$ lower alkyl, phenyl, benzyl, or C$_{3-8}$ cycloalkyl, any of which R groups may be substituted by one to three substituents, same or different, selected from the group consisting of halo, hydroxy, C$_{1-8}$ alkoxy, —NH$_2$, —C(O)NH$_2$, —CH(O), —C(O)OH and —NO$_2$:

X is a pharmaceutically acceptable cation, a pharmaceutically acceptable metal center, or a pharmaceutically acceptable organic group, selected from the group consisting of C$_{1-8}$ lower alkyl, —C(O)CH$_3$ and —C(O)NH$_2$;

Y is one to three, consistent with the valence of X; and (II) a pharmaceutically acceptable carrier therefor.

12. The composition of claim 11, wherein R is a branched chain lower alkyl group having 3–6 carbon length, optionally substituted by one to three substituents, same or different, selected from the group consisting of halo, hydroxyl, —NH$_2$, —CH(O) and —C(O)OH.

13. The composition of claim 11, wherein R is C$_{3-8}$ cycolalkyl, optionally substituted by one to three substituents, same or different, selected from the group consisting of halo, —NH$_2$, hydroxy, —CH(O), and —C(O)OH.

14. The composition of claim 11, wherein R is isopropyl.

15. The composition of claim 11, wherein said composition is suitable for intravenous injection.

16. The composition of claim 11, wherein R is isopropyl, and said composition is suitable for intravenous injection.

17. The composition of claim 11, wherein X is a pharmaceutically acceptable cation.

18. The composition of claim 17, wherein R is a branched chain lower alkyl group having 3–6 carbon length, optionally substituted by one to three substituents, same or different, selected from the group consisting of halo, hydroxyl, —NH$_2$, —CH(O) and —(O)OH.

19. The composition of claim 17, wherein R is isopropyl.

20. The composition of claim 17, wherein said composition is suitable for intravenous injection.

* * * * *

UNITED STATES PATENT AND TRADEMARK OFFICE
CERTIFICATE OF CORRECTION

PATENT NO. : 4,954,526

Page 1 of 3

DATED : September 4, 1990

INVENTOR(S) : Larry K. Keefer, Tambra M. Dunams, Joseph A. Hrabie and David A. Wink It is certified that error appears in the above-identified patent and that said Letters Patent is hereby corrected as shown below:

Column 1, Line 7:
change "oxide nucleophile" to --oxide-nucleophile--

Column 1, Line 59:
change "loweralkyl acyl" to --loweralkyl, acyl--

Column 2, Line 37:
change "[as used herein means -C(O)NH$_2$" to --as used herein means -C(O)NH$_2$.--

Column 2, Line 38:
change "-CH(O)." to ---CH(O).--

Column 2, Line 68, delete "," after comptability.

Column 3, Line 15:
change "-O-CH$_2$H$_5$-O-loweralkyl." to ---O-C$_2$H$_5$, and -O-loweralkyl.--

Column 4, Line 19:
Change "plexes," to --plexes' --

Column 4, Line 21:
Change "M +" to --M$^+$ --

Column 4, Lines 23-24:
delete text in its entirety and replace with correct text:

Column 4, Line 63:
Change "Isooroovlamine" to --Isopropylamine--
Change "isooroovlammonium" to --isopropylammonium--

Column 4, Line 64:
Change "complex 1:11" to --complex 1:1

Column 4, line 65:
Change "(CH$_3$)$_2$CHNH$_3$$^+$ O-" to (CH$_3$)$_2$CHNH$_3$$^+$ $^-$O- --

Column 5, Line 1:
Change "(196)," to --(1961), --

UNITED STATES PATENT AND TRADEMARK OFFICE
CERTIFICATE OF CORRECTION

PATENT NO. : 4,954,526

DATED : September 4, 1990

Page 2 of 3

INVENTOR(S) : Larry K. Keefer, Tambra M. Dunams, Joseph A. Hrabie and David A. Wink It is certified that error appears in the above-identified patent and that said Letters Patent is hereby corrected as shown below:

Column 5, Line 11:
change "Isooroovlamine" to --Isopropylamine--

Column 5, Line 39:
change " $[(C_2H_5)CH_3)CH]$ $NH_3^+$ " to -- $(C_2H_5)(CH_3)CH]$ $NH_3^+$ --

Column 5, Line 40:
Paragraph should be in normal type with centered heading --Preparation IV"--.

Column 6, Line 8:
change "Preparation VI" centered

Column 6, Line 28:
change "compounds," to --compounds'--

Column 7, Line 18: (second occurrence)
change " n-$c_4H_9$)," to --n-$C_4H_9$), --

Column 7, Line 23:
change "$Na^+$--O" to --$Na^+$ $^-$O--

Column 7, Line 27:
change "$(C_6H_5)CH_2$" to --$(C_6H_5)CH_2-NH_3^{+-}O-N(NO)N(H)(-CH_2(C_6H_5))$, --

Column 7, Line 28: delete entire line and replace as follows:
--$(C_6H_{11})CH-NH_3^{+-}O-N(NO)N(H)(-CH_2-(C_6H_{11}))$.--

Column 7, Lines 30-31: Delete in their entirety.

Column 8, Line 58:
change "cycolal-" to --cycloal- --

Column 9, Line 9:
change "-CH(CO)" to ---CH(O)--

Column 9, Line 38:
change :-$NO_2$:" to -- -$NO_2$; --

Column 10, Line 33:
change "-(O)OH" to ---C(O)OH --

UNITED STATES PATENT AND TRADEMARK OFFICE
CERTIFICATE OF CORRECTION

PATENT NO. : 4,954,526

DATED : September 4, 1990

INVENTOR(S) : Larry K. Keefer, Tambra M. Dunams, Joseph A. Hrabie and David A. Wink It is certified that error appears in the above-identified patent and that said Letters Patent is hereby corrected as shown below:

On the title page item [19] change "Keefer" to --Keefer et al--.
On the title page item [75] Inventor: change "Larry K. Keefer, Bethesda, Md." to --Larry K. Keefer, Bethesda, Md.; David Anderson Wink, Frederick, Md.; Tambra Marie Dunams, Frederick, Md.; Joseph Anthony Hrabie, Frederick, Md.--.

Signed and Sealed this

Fifth Day of May, 1992

*Attest:*

DOUGLAS B. COMER

*Attesting Officer*  *Acting Commissioner of Patents and Trademarks*